United States Patent
Patel et al.

(10) Patent No.: US 11,960,013 B2
(45) Date of Patent: Apr. 16, 2024

(54) MOTION CAPTURE SYSTEM AND METHOD

(71) Applicant: University of Cape Town, Cape Town (ZA)

(72) Inventors: Amir Patel, Cape Town (ZA); Do Yeou Ku, Cape Town (ZA)

(73) Assignee: University of Cape Town, Capetown (ZA)

(*) Notice: Subject to any disclaimer, the term of this patent is extended or adjusted under 35 U.S.C. 154(b) by 177 days.

(21) Appl. No.: 16/980,743

(22) PCT Filed: Mar. 14, 2019

(86) PCT No.: PCT/IB2019/052087
§ 371 (c)(1),
(2) Date: Sep. 14, 2020

(87) PCT Pub. No.: WO2019/175831
PCT Pub. Date: Sep. 19, 2019

(65) Prior Publication Data
US 2021/0003717 A1     Jan. 7, 2021

(30) Foreign Application Priority Data
Mar. 14, 2018   (IT) .......................... 102018000003543

(51) Int. Cl.
*G01S 19/43*     (2010.01)
*G01S 19/49*     (2010.01)
(Continued)

(52) U.S. Cl.
CPC .............. *G01S 19/43* (2013.01); *G01S 19/49* (2013.01); *G06F 3/011* (2013.01); *G01S 19/19* (2013.01)

(58) Field of Classification Search
CPC .......... G01S 19/43; G01S 19/19; G01S 19/49; G06F 3/011
See application file for complete search history.

(56) References Cited

U.S. PATENT DOCUMENTS

2005/0047275 A1* 3/2005 Chamberlain ........... G01V 1/22
                                                        367/56
2010/0318294 A1* 12/2010 Rosing ................ G01C 21/165
                                                        701/500
(Continued)

FOREIGN PATENT DOCUMENTS

WO     WO 1996/029679 A1 *  9/1996    ............... G06T 7/20
WO     WO-2006086439 A2     8/2006
(Continued)

OTHER PUBLICATIONS

Lightbody et al. ( Techniques in Relative RTK GNSS Positioning, 2010, Trimble Marine Division) (hereinafter Lightbody). (Year: 2010).*

(Continued)

*Primary Examiner* — Elias Desta
(74) *Attorney, Agent, or Firm* — Morrison & Foerster LLP (57) ABSTRACT

A motion capture system and method are provided. In a motion capture method, a plurality of motion datasets are accessed. Each motion dataset is associated with a motion sensing unit at which timestamped motion data points of that motion dataset are generated, each motion sensing unit is configured to be in physical contact with a different part of a body of interest. Each timestamped motion data point is timestamped at the motion sensing unit at which it is generated using a clock time that is synchronized across the plurality of motion sensing units. The timestamped motion data points are processed to generate a kinematic model which describes motion of the respective parts of the body of interest.

11 Claims, 3 Drawing Sheets

(51) Int. Cl.
  *G06F 3/01* (2006.01)
  *G01S 19/19* (2010.01)

(56) References Cited

U.S. PATENT DOCUMENTS

| | | | |
|---|---|---|---|
| 2013/0030700 A1 | 1/2013 | Miller et al. | |
| 2016/0210838 A1* | 7/2016 | Yan | G08B 25/001 |
| 2017/0084070 A1 | 3/2017 | Chamdani et al. | |
| 2017/0344919 A1 | 11/2017 | Chang et al. | |

FOREIGN PATENT DOCUMENTS

| | | |
|---|---|---|
| WO | WO-2008127316 A1 | 10/2008 |
| WO | WO-2012082615 A2 | 6/2012 |
| WO | WO-2016081778 A1 | 5/2016 |

OTHER PUBLICATIONS

International Search Report and Written Opinion dated Jul. 2, 2019, for PCT Patent Application No. PCT/IB2019/052087 filed on Mar. 14, 2019, 11 pages.

\* cited by examiner

MOTION CAPTURE SYSTEM AND METHOD

CROSS-REFERENCE(S) TO RELATED APPLICATIONS

This application is a national stage application under 35 U.S.C. § 371 of International application No. PCT/IB2019/052087, filed internationally on Mar. 14, 2019, which claims priority from Italian patent application number IT 102018000003543, filed on Mar. 14, 2018, the disclosures of which are herein incorporated by reference in their entireties.

FIELD OF THE INVENTION

This invention relates to a motion capture system and method. The invention may find application in the field of biomechanical motion capture.

BACKGROUND TO THE INVENTION

The term "motion capture" (or, in some fields, "motion tracking") typically refers to the process of recording the movement of objects or people and can find application in military, entertainment, sports, medicine and the like. Example entertainment applications include filmmaking and video game development in which actions of human actors are recorded and used to animate digital character models in 2D or 3D computer animation.

Another field of application of motion capture is biomechanics, which relates to the study of the mechanical laws relating to the movement or structure of living organisms. Subfields of biomechanics include kinesiology, animal locomotion and gait analysis, musculoskeletal and orthopaedic biomechanics, sports biomechanics and the like. Integral to this field of study is the ability to capture accurately the motion of bodies of interest and, more particularly, to respective parts (e.g. limbs, feet, hands, head, etc.) of a body of interest relative to each other.

Existing motion capture systems are typically either optical or inertial measurement unit-based. Optical systems typically include many cameras which record images from which kinematic models may be built. Optical systems may be advantageous in that they are accurate, but suffer the disadvantages of being expensive and restrictive in terms of the limited volume in which motion can be captured (e.g. typically a single room).

Inertial measurement unit (IMU) systems may typically include many sensors which are fitted to respective parts of a body of interest. The sensors quantify inertial measurement data which can be used to build a kinematic model of the body of interest. Inertial measurement unit systems may provide advantages in the form of greater portability, but are typically less accurate than optical systems as the inertial measurements are prone to drift and adequate time synchronisation of data from the multiple sensors is difficult.

There is accordingly scope for improvement.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

A computer-implemented method comprising: accessing a plurality of motion datasets, each motion dataset being associated with a motion sensing unit at which timestamped motion data points of that motion dataset are generated, wherein each motion sensing unit is configured to be in physical contact with a different part of a body of interest; processing the timestamped motion data points to generate a kinematic model which describes motion of the respective parts of the body of interest; and, outputting the kinematic model, wherein each timestamped motion data point is timestamped at the motion sensing unit at which it is generated using a clock time that is synchronized across the plurality of motion sensing units using a satellite network.

A further feature provides for the satellite network to be a global navigation satellite systems (GNSS) network.

Still further features provide for each motion sensing unit to include a plurality of disparate sensors and for each motion dataset to include timestamped motion data points from each of the plurality of disparate sensors.

Yet further features provide for the method to include pre-processing the timestamped motion data points using a pre-processing algorithm, and filtering the timestamped motion data points to construct a three-dimensional trajectory of the part of the body in question.

Further features provide for filtering the timestamped motion data points to include, for each motion dataset, inputting the timestamped motion data points from the disparate sensors into the filtering algorithm which outputs a single series of filtered motion data points for that motion dataset.

Still further features provide for the method to include applying a structural model associated with the body of interest to the timestamped motion data points, for the structural model to define theoretical kinematic constraints associated with respective parts of the body of interest as additional information for filtering of the motion data points.

Yet further features provide for the filtering algorithm to be a non-linear least squares estimation algorithm; and, for the filtering algorithm to be an extended Kalman filter.

Further features provide for the method to include: accessing a reference dataset including reference data points having been measured at a base unit, wherein the position of the base unit is fixed; and, using the reference dataset to correct errors present in the motion datasets; and, for using the reference dataset to correct errors to include applying real time kinematic techniques.

Yet further features provide for the timestamped motion data points of each motion dataset to include global navigation satellite systems-based motion data points and for applying real time kinematic techniques to enhance precision of the global navigation satellite systems-based motion data points.

The body of interest may be a human or animal body and the structural model may be a skeletal model.

In accordance with a further aspect of the invention there is provided a method conducted at a motion sensing unit configured to be in physical contact with a part of a body of interest, the method comprising: receiving, from a sensor, motion data points relating to motion of the sensor; receiving, from a satellite network sensor, a satellite network signal including timing information; using the satellite network timing information to synchronise a local clock time maintained by the motion sensing unit with clock times of a plurality of other motion sensing units in a sensor network; timestamping the motion data points to generate timestamped motion data points; and, providing a motion dataset including the timestamped motion data points to a computing device, wherein the motion dataset is provided to the computing device for filtering together with motion datasets from the other motion sensing units in the sensor network to generate a kinematic model which describes motion of the respective parts of the body of interest.

In accordance with a further aspect of the invention there is provided a system comprising: a processor and a memory configured to provide computer program instructions to the processor to execute functions of components; a motion dataset accessing component for accessing a plurality of motion datasets, each motion dataset being associated with a motion sensing unit at which timestamped motion data points of that motion dataset are generated, wherein each motion sensing unit is configured to be in physical contact with a different part of a body of interest; a processing component for processing the timestamped motion data points to generate a kinematic model which describes motion of the respective parts of the body of interest; and, a model outputting component for outputting the kinematic model, wherein each timestamped motion data point is timestamped at the motion sensing unit at which it is generated using a clock time that is synchronized across the plurality of motion sensing units using a satellite network.

Further features provide for the system to include a plurality of motion sensing units, each motion sensing unit including a plurality of disparate sensors and for each motion dataset to include timestamped motion data points from each of the plurality of disparate sensors.

Still further features provide for the satellite network to be a global navigation satellite systems (GNSS) network and for each motion sensing unit to include a global navigation satellite systems network receiver.

A yet further feature provides for the system to include a base unit and a correction component, including: a reference dataset accessing component for accessing a reference dataset including reference data points having been generated at the base unit, wherein the position of the base unit is fixed; and, an error correcting component for using the reference dataset to correct errors introduced into the motion datasets.

In accordance with a further aspect of the invention there is provided a motion sensing unit configured to be in physical contact with a part of a body of interest and comprising: a sensor for providing motion data points relating to motion of the sensor; a satellite network sensor for receiving a satellite network signal including timing information; a clock synchronisation component for using the satellite network signal to synchronise a local clock time maintained by the motion sensing unit with clock times of a plurality of other motion sensing units in a sensor network; a timestamping component for timestamping the motion data points to generate timestamped motion data points; and, a providing component for providing a motion dataset including the timestamped motion data points to a computing device, wherein the motion dataset is provided to the computing device for processing together with motion datasets from the other motion sensing units in the sensor network to generate a kinematic model which describes motion of the respective parts of the body of interest.

In accordance with a further aspect of the invention there is provided a sensor network including a plurality of motion sensing units as defined above.

In accordance with a further aspect of the invention there is provided a computer program product comprising a computer-readable medium having stored computer-readable program code for performing the steps of: accessing a plurality of motion datasets, each motion dataset being associated with a motion sensing unit at which timestamped motion data points of that motion dataset are generated, wherein each motion sensing unit is configured to be in physical contact with a different part of a body of interest; processing the timestamped motion data points to generate a kinematic model which describes motion of the respective parts of the body of interest; and, outputting the kinematic model, wherein each timestamped motion data point is timestamped at the motion sensing unit at which it is generated using a clock time that is synchronized across the plurality of motion sensing units using a satellite network.

Further features provide for the computer-readable medium to be a non-transitory computer-readable medium and for the computer-readable program code to be executable by a processing circuit.

Embodiments of the invention will now be described, by way of example only, with reference to the accompanying drawings.

DETAILED DESCRIPTION WITH REFERENCE TO THE DRAWINGS

A sensor network and associated system and method for capturing the motion of a body of interest are described. The sensor network and associated system and method may find application in capturing the motion of any body of interest having respective parts which move relative to each other. Exemplary applications include biomechanical motion capture (for example, for the generation of kinematic models which describe the motion of humans or animals), mechanical motion capture (for example capturing the motion of buildings due to wind, earthquakes, heating and cooling effects, etc.), geo-mechanical motion capture (e.g. monitoring wall movement in open cast mines) and the like. In some embodiments described herein, satellite network-based time synchronisation, a motion capture sensor network may be provided. Embodiments may provide a GPS-time synchronised motion capture sensor and associated sensor network.

Figure 1:
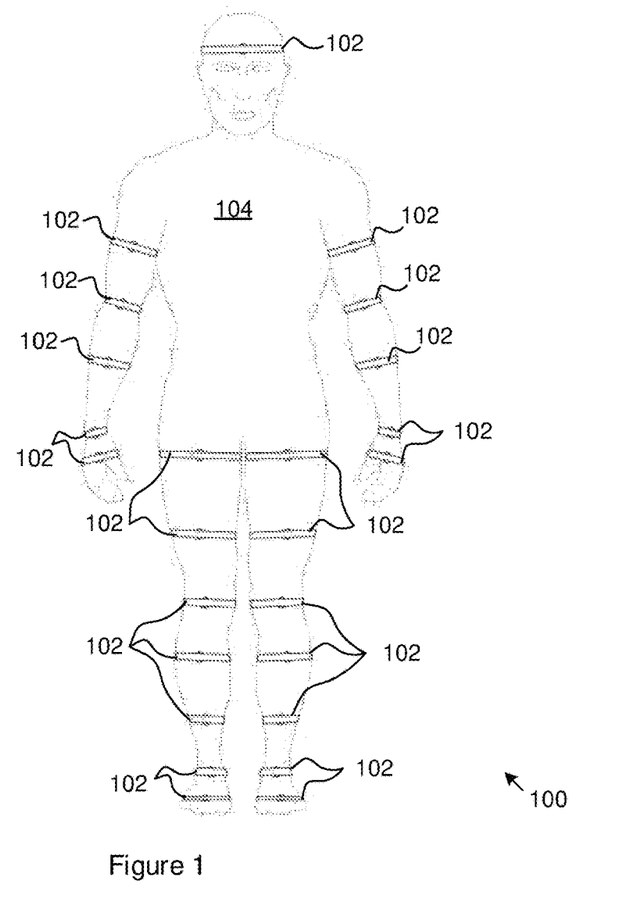
FIG. 1 is a schematic diagram which illustrates an example of a sensor network according to aspects of the present disclosure.

FIG. 1 is a schematic diagram which illustrates an example of a sensor network (100) according to aspects of the present disclosure. The sensor network (100) may include a plurality of motion sensing units (102). Each motion sensing unit (102) may be configured to be in physical contact with a body of interest (104), which in the example embodiment illustrated is a human being.

Each motion sensing unit may include a plurality of disparate sensors (such as accelerometers, gyroscopes, magnetometers, etc.) and may be configured to record motion data points measured by the sensors and which relate to its motion (and in turn to the motion of the respective part of the body of interest (104) to which it is attached). Exemplary parameters to which the motion data points may relate include acceleration along and rotation about each of three axes, positioning information (e.g. geographical location coordinates), barometric pressure, Hall resistance and the like.

Each motion sensing unit may be configured to maintain a local clock time. The clock time of each motion sensing unit (102) may be synchronised across the entire sensor network (100) using a suitable satellite network, such a GNSS network. Each motion sensing unit (102) may be configured to timestamp the recorded motion data points using the local clock time of that motion sensing unit (102) to generate timestamped sensor data points.

In some implementations, the motion sensing units (102) may operate wirelessly. A battery or other power source may be provided and the motion sensing units (102) may either wireless transmit the timestamped data points or store them internally for subsequent acquisition (e.g. after motion capture).

With the motion sensing units (102) fitted to various parts of the body of interest (104), the timestamped motion data points measured by each motion sensing unit (102) can be processed to determine the motion of respective parts of the body of interest. For example, in the case of a human being, one or more motion sensing units (102) can be fixed to each foot, leg, hand and arm as well as to the torso, head, neck, shoulders and the like. In a biomechanical motion capture implementation, the motion sensing units (102) may be configured to be fixed to parts of the body which are proximate joints (e.g. in the case of a human body of interest, knees, ankles, hips, elbows, wrists, shoulders, neck, etc.).

In the case of a biomechanical implementation, the motion sensing units may be lightweight, for example in the order of 30 g or less per unit (preferably the total mass of sensor network attached to the body of interest should be less than 10% of the mass of the body of interest), and may be physically small, for example having a diameter of about 40 mm or less and a depth of about 10 mm or less.

Figure 2:
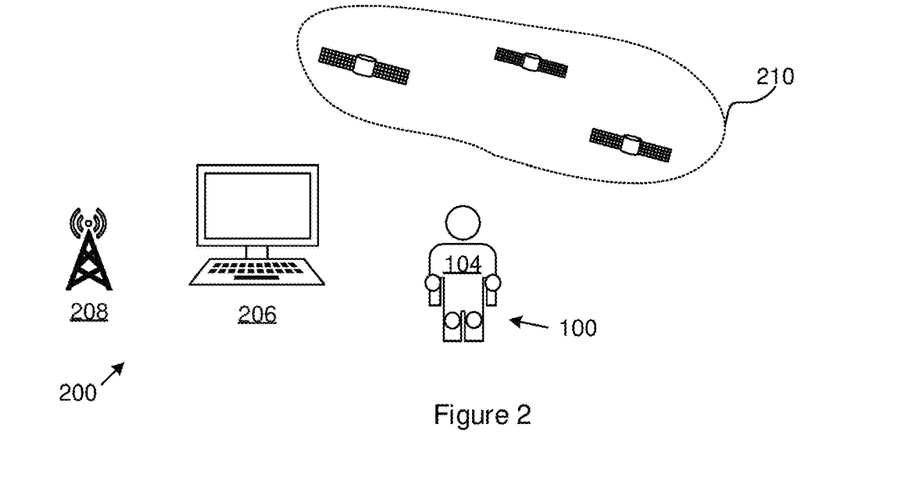
FIG. 2 is a schematic diagram which illustrates an exemplary motion capture system according to aspects of the present disclosure.

FIG. 2 is a schematic diagram which illustrates an exemplary motion capture system (200) according to aspects of the present disclosure. The system (200) may include a sensor network (100) including a plurality of motion sensing units (102), such as that described above with reference to FIG. 1. The system (200) may also include a computing device (206).

The computing device (206) may be any appropriate electronic device capable of interfacing with the motion sensing units (102). The computing device (206) may be configured to access the timestamped motion data points generated by each of the motion sensing units (102). The computing device (206) may be configured to process the timestamped data points to generate a kinematic model which describes motion of the respective parts of the body of interest (104). The computing device (206) may be configured to output the kinematic model, for example, to a display for analysis by a user.

In some implementations, the system (200) may include a base unit (208). The base unit (208) may be configured to measure reference data points. The reference data points may be suitable for correcting errors introduced into the motion data points measured by the motion sensing units (102). When using the system, the location and/or positioning of the base unit (208) may be fixed, for example in relation to the earth, and the reference data points may be usable in detecting and correcting for noise introduced into the data points measured by the motion sensing unit and/or the base unit. The base unit may be required to be within a minimum radius of the sensor network (100), for example within 10 km or the like. The base unit (208) may measure the reference data points using signals received from a satellite network (210).

For example, as will be explained in greater detail below, the satellite network (210) may be a regional or global navigation satellite system and the reference data points measured by the base unit (208) may be used to implement real time kinematic (RTK), or similar, techniques to reduce, correct or compensate for noise introduced into the motion data points by atmospheric and other effects.

By providing a base unit (208), the accuracy of the kinematic model generated and output by the computing device (206) may be improved.

The system (200) described above may implement a motion capture method. An exemplary motion capture method is illustrated in the flow diagram of FIG. 3. The method may be conducted by the computing device (206).

Figure 3:
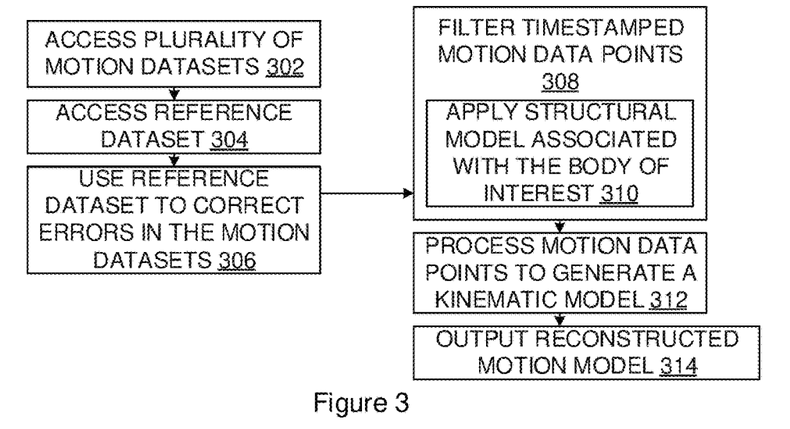
FIG. 3 is a flow diagram which illustrates an exemplary motion capture according to aspects of the present disclosure.

The method may include accessing (302) a plurality of motion datasets. Each motion dataset may be associated with a motion sensing unit (102) which is fixed or attached to a different part of the body of interest (104)—as illustrated best in FIG. 1. Each motion dataset may include timestamped motion data points which have been generated at the motion sensing unit (102) with which the motion dataset is associated.

The timestamped motion data points may have been timestamped at the motion sensing unit at which they are generated using a clock time that is synchronized, using a satellite network (210), across the plurality of motion sensing units. The satellite network may be a global or regional navigation satellite system network (such as GPS, GLONASS, etc.).

As mentioned above, each motion sensing unit (102) may include a plurality of disparate sensors and each motion dataset may include motion data points having been measured or obtained from each of the plurality of disparate sensors. In some implementations, the timestamped motion data points of each motion dataset may include global or regional navigation satellite systems-based motion data points (such as GPS data points)

Accessing (302) the plurality of motion datasets may include receiving the timestamped motion data points from the respective motion sensing units (102) via a suitable wired or wireless communication link. Accessing the plurality of motion datasets may include receiving the motion data points in real-time (e.g. live-streamed), as they are recorded and timestamped by the respective motion sensing unit (102) or at a later stage for post-processing (e.g. as a batch). For example in some implementations the motion sensing units (102) may store the timestamped motion data points for access by the computing device at a later stage and accessing the motion datasets may include accessing the motion datasets from respective memory modules of the motion sensing units or the like.

The method may include accessing (304) a reference dataset. The reference dataset may include reference data points having been measured at the base unit (208). As mentioned above, the position of the base unit (208) is fixed with reference to, for example, the surface of the earth. As with the motion datasets, accessing the reference data points may include accessing the reference data points via a suitable wired or wireless communication link in real-time or as a batch of reference data points, possibly in post-processing. The reference data points may be timestamped at the base unit (208) using a clock time maintained by the base unit (208) which is synchronised to the plurality of motion datasets using the satellite network (210).

The method may include using (306) the reference dataset to correct errors present in the motion datasets. In some implementations, using (306) the reference dataset to correct errors includes applying real time kinematic techniques to correct for errors.

For example, the data points measured at each motion sensing unit (102) as well as the base unit (208) may include satellite network-based data points. Using real time kinematic techniques may use measurements of the phase of the satellite network signal's carrier wave as well as or in place of the information content of the signal. The reference dataset from the base unit (acting as a reference station) is used to provide real-time corrections to the corresponding data points measured by the respective motion sensing units (102). Using real time kinematics, also referred to as Carrier-Phase Enhancement (or CPGPS), may provide up to centimetre-level accuracy for the satellite network-based data points. Applying real time kinematic techniques may therefore enhance precision of the satellite network-based motion data points.

Using real time kinematic techniques may include extracting the phase of the carrier of the satellite network signals received at the base unit (208) and providing this data (e.g. as the reference data points) to the computing device and/or the individual motion sensing units (102) which may then compare the respective phase measurements of each motion sensing unit with those of the base unit (208). By knowing that the base unit (208) is stationary, errors inherent in the satellite network signal can be estimated and/or eliminated. In some implementations, real time kinematic correction may be performed in real time at each of the motion sensing units (in which case a suitable wireless communication link may be provided between the base unit and the motion sensing units) while in other implementations real time kinematic technique-based correction may be performed as post-processing at the computing device (206).

The method may include filtering (308) otherwise pre-processing the timestamped motion data points. Filtering (308) the timestamped motion data points may, for each motion dataset, include combining the timestamped motion data points from the disparate sensors of the motion sensing unit (102) with which that dataset is associated to provide a single series of filtered motion data points for that motion dataset. Filtering or otherwise pre-processing the timestamped motion data points may accordingly include performing a data or sensor fusion operation on the data points. Filtering may be performed on the corrected data points (i.e. on which real time kinematic processing has been performed).

Filtering (308) or otherwise pre-processing the data points may include outputting a filtered series of filtered data points for each motion sensing unit (and hence for each motion dataset). In some implementations, the filtered series of data points may represent a three-dimensional trajectory of the body part with which the series of data points is associated. It should be appreciated that any appropriate filtering or pre-processing algorithm may be used. In some implementations, a suitable non-linear least squares estimation algorithm, such as the extended Kalman filter, may be used to filter the timestamped motion data points although in other implementations other suitable filtering or pre-processing and/or data fusion techniques may be implemented.

The method may include applying (310) a structural model associated with the body of interest to the filtered and/or timestamped motion data points. The structural model may for example define theoretical kinematic constraints associated with respective parts of the body, such as arm movement constraints, degree of knee bend constrains or the like, and applying (310) the structural model may include using the structural model as a gating function to identify invalid timestamped motion data points.

Applying (310) the structural model may be done as a part of the filtering (308) or pre-processing of the timestamped motion data points. The structural model may for example define theoretical kinematic constraints associated with respective parts of the body and applying (310) the structural model may include providing these constraints as additional information during filtering or pre-processing of the motion data points. In the case of least squares estimation for example, applying (310) the structural model may include inputting theoretical kinematic constraints associated with respective parts of the body into the filtering or pre-processing algorithm to provide additional information for derivation of the least squares estimate.

In implementations in which the body of interest (104) is that of a human or animal, the structural model may be a skeletal model.

The method may include processing (312) the motion data points to generate a kinematic, or reconstructed motion, model which describes motion of the respective parts of the body of interest (104). Processing (312) the motion data points may include processing the one or more of the timestamped motion data points, the filtered motion data points and the corrected motion data points. Processing the motion data points may include mapping a three dimensional skeletal model associated with the body of interest to the motion data points such that the respective parts of the skeletal model are manipulated based on the trajectories data points associated with those parts. Processing the motion data points may include determining position and velocity of the respective parts of the body of interest relative. The position and velocity determined may be absolute or relative to other parts of the body of interest.

Processing (312) the motion data points may further include comparing trajectory data for each of the motion sensing units and hence for each of the parts of the body of interest to determine or estimate biomechanical parameters, such as joint torque, ground reaction forces, and the like. Processing (312) the motion data points may further include detecting injuries to the body of interest (104), monitoring recovery from injury (e.g. by comparing various sets of motion data points collated over time), performance improvement and the like.

The method may include outputting (314) the kinematic model and/or other biomechanical parameters, for example to a display associated with the computing device (206).

Figure 4:
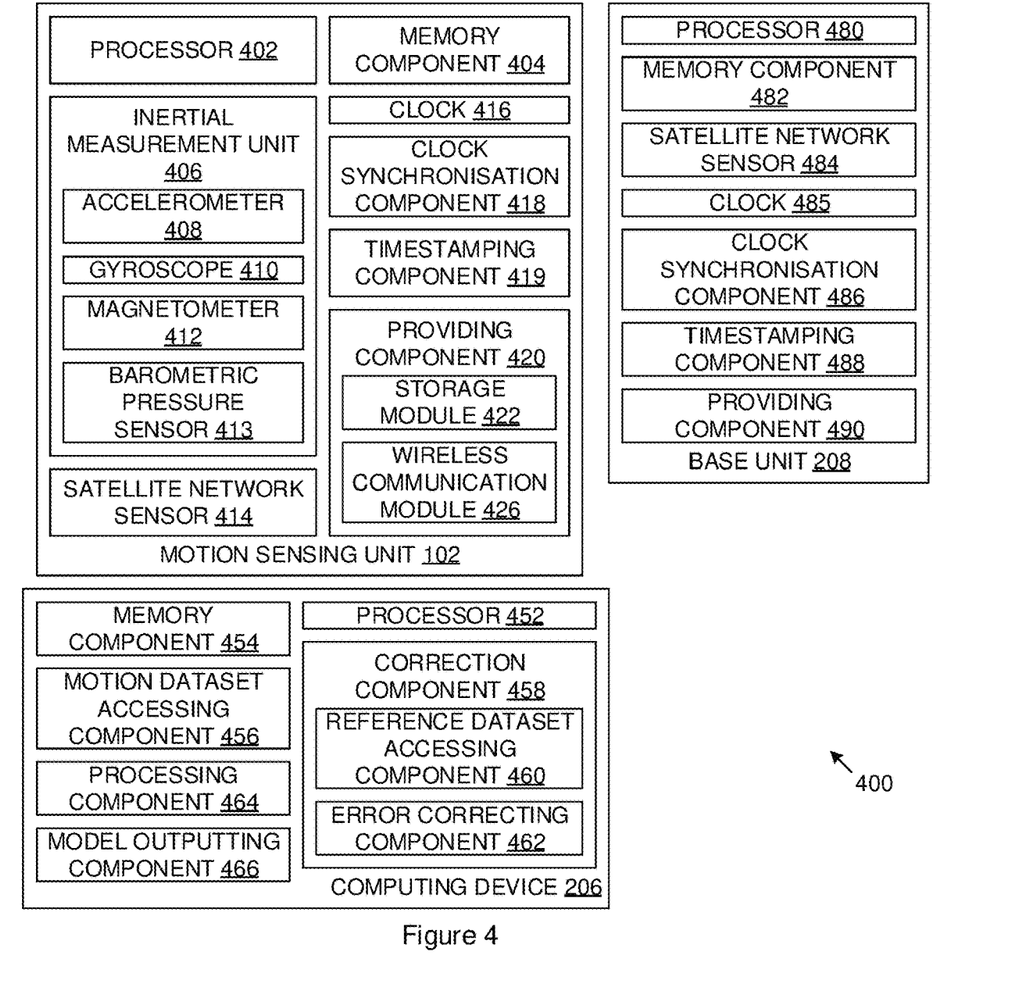
FIG. 4 is a block diagram which illustrates exemplary components which may be provided by a motion capture system according to aspects of the present disclosure.

Various components may be provided for implementing the method described above with reference to FIG. 3. FIG. 4 is a block diagram which illustrates exemplary components which may be provided by a motion capture system (400). The system (400) may include a motion sensing unit (102), a computing device (206) and a base unit (208).

The motion sensing unit (102) may include a processor (402) for executing the functions of components described below, which may be provided by hardware or by software units executing on the motion sensing unit (102). The processor (402) may be any suitable processor and in some implementations may, for example, include a 48 MHz clock or other external crystal oscillator, a real time clock and various communication interfaces (such as SPI, SD, UART, etc.). It will, however, be apparent to those skilled in the art that the frequency of the clock may be altered depending, amongst other factors, on the type of application for which it is used.

The software units may be stored in a memory component (404) and instructions may be provided to the processor (402) to carry out the functionality of the described components.

The motion sensing unit (102) may include a plurality of disparate sensors arranged to provide motion data points relating to motion of the respective sensors. For example, the motion sensing unit (102) may include an inertial measurement unit (406), which may include one or more of an accelerometer (408), a gyroscope (410), a magnetometer (412) and a barometric pressure sensor (413). The inertial measurement unit (406) may be arranged to measure parameters and output motion data points associated with those parameters, such as acceleration, rate of rotation, magnetic force, atmospheric pressure, inertial measurement unit drift error factor, inertial measurement unit temperature variation factor, hall resistance, magnetometer calibration factor, barometric pressure sensor data, barometric pressure sensor drift error, barometric pressure sensor temperature variation factor and the like.

The motion sensing unit (102) may include a satellite network sensor (414) arranged to receive signals and/or data transmitted from a satellite network (210). The satellite network sensor (414) may for example be a GPS, GLONASS, etc. receiver arranged to receive signals and/or data from GPS, GLONASS, etc. satellites and to use these signals to determine the geographical position of the sensor. In some implementations, the satellite network sensor (414) may be an RTK-GPS sensor with a time synchronisation functionality. The satellite network sensor (414) may be arranged to measure and/or determine parameters and to output motion sensing data points associated with those parameters, such as satellite signal data, geographical location data (e.g. positioning coordinates), raw data messages (e.g. GPS-RAWX or other observation and navigation data/information), GPS-NMEA messages, timing data (e.g. second satellite timing data such as a one pulse per second (PPS) signal) received or derived from the satellite network and the like.

The motion sensing unit (102) may have a clock (416) which maintains a clock time. The clock may be a part of or separate from the processor (402). The clock (416) may include or otherwise make use of a suitable crystal, such as a 32.768 kHz crystal. The motion sensing unit may also have a clock synchronisation component (418) which is arranged to use timing data determined by the satellite sensor network (such as the PPS signal) to synchronise the clock time with that which is maintained by other motion sensing units (102) in the sensor network (100). The clock synchronisation component (418) may be arranged to synchronise the clock time to the nearest nanosecond.

The motion sensing unit (102) may include a timestamping component (419) arranged to use the synchronised clock time to timestamp motion data points measured or otherwise obtained by the various sensors and to output timestamped motion data points.

The motion sensing unit (102) may include a providing component (420) arranged to provide the timestamped motion data points and/or other data measured or determined by the various sensors to the computing device (206). In some implementations, the providing component (420) may interact with a storage module (422) which is configured to store the timestamped motion data points and/or other data for subsequent retrieval by the computing device. The storage module (422) may for example be provided by a flash memory module and associated connector (e.g. a USB port), removable memory card (e.g. a SECURE DIGITAL® memory card, etc.) or the like. In other implementations, the providing component (420) may interact with a wireless communication module (426) (e.g. BLUETOOTH®, or similar) arranged to transmit data to and/or receive data from the computing device (206) using a suitable wireless communication interface.

The computing device (206) may include a processor (452) for executing the functions of components described below, which may be provided by hardware or by software units executing on the computing device (206). The software units may be stored in a memory component (454) and instructions may be provided to the processor (452) to carry out the functionality of the described components. In some cases, for example in a cloud computing implementation, software units arranged to manage and/or process data on behalf of the computing device (206) may be provided remotely.

The computing device (206) may include a motion dataset accessing component (456) arranged to access a plurality of motion datasets. Each motion dataset may be associated with a motion sensing unit (102) at which timestamped motion data points of that motion dataset are generated. Each timestamped motion data point may be timestamped at the motion sensing unit (102) at which it is generated using a clock time that is synchronized across the plurality of motion sensing units using the satellite network (210).

The computing device (206) may include a correction component (458), which may include a reference dataset accessing component (460) arranged to access a reference dataset. The reference dataset may include reference data points having been generated at the base unit (208). The correction component (458) may include an error correcting component (462) arranged to use the reference dataset to correct errors introduced into the motion datasets.

The computing device (206) may include a processing component (464) arranged to process the timestamped motion data points and/or reference data points to generate a kinematic model which describes motion of the respective parts of the body of interest to which the motion sensing units (102) are fixed. The processing component (464) may include a structural model applying component arranged to apply a structural model to the timestamped and/or processed motion data points.

The computing device (206) may further include a model outputting component (466) arranged to output the kinematic model.

The computing device (206) may further include components arranged to provide the functionality of the method described above with reference to FIG. 3.

The base unit (208) may include some or all of the components of the motion sensing unit to enable the base unit (208) to provide the functionality described herein. In some implementations, the base unit may include a processor (480) and memory component (482). The base unit (208) may further include a satellite network sensor (484), clock (485), clock synchronisation component (486), timestamping component (488) and providing component (490), which may provide functionality corresponding to those components of the motion sensing unit (102).

Embodiments described herein may provide a motion sensing unit which includes an Inertial Measurement Unit (IMU), RTK-enabled GPS sensor, barometric pressure sensor and SD card logger. Multiple motion sensing units may be synchronised via GPS-time (to nanosecond accuracy) and may be deployed on the limbs of a test subject (human or animal). This motion sensing unit data may be post-processed using a fusion algorithm to determine the kinematics (position and velocity) of the limbs in a fashion that is normally done using static cameras. These estimates can also be used to estimate the joint torque and ground reaction forces (GRF) of the subject. It should be appreciated that in a preferred embodiment the satellite network sensor may be a RTK-enabled GPS sensor. RTK-enabled GPS sensors may typically be equipped with a time synchronization functionality enabling the sensors to measure actual satellite signal data which provides sub-cm accuracy. This may differ from most other known GPS/IMU sensor combinations which typically only measure the geographical location data resulting in a measurement accuracy of approximately 5 m.

It should further be appreciated that the time synchronization functionality allows the sensors to be synchronised independently, resulting in the sensors being infinitely scalable. Most sensors in existing systems synchronise via standard wireless modules, such as Bluetooth™, which may provide less accurate measurements due to the slower synchronisation speeds.

Figure 5:
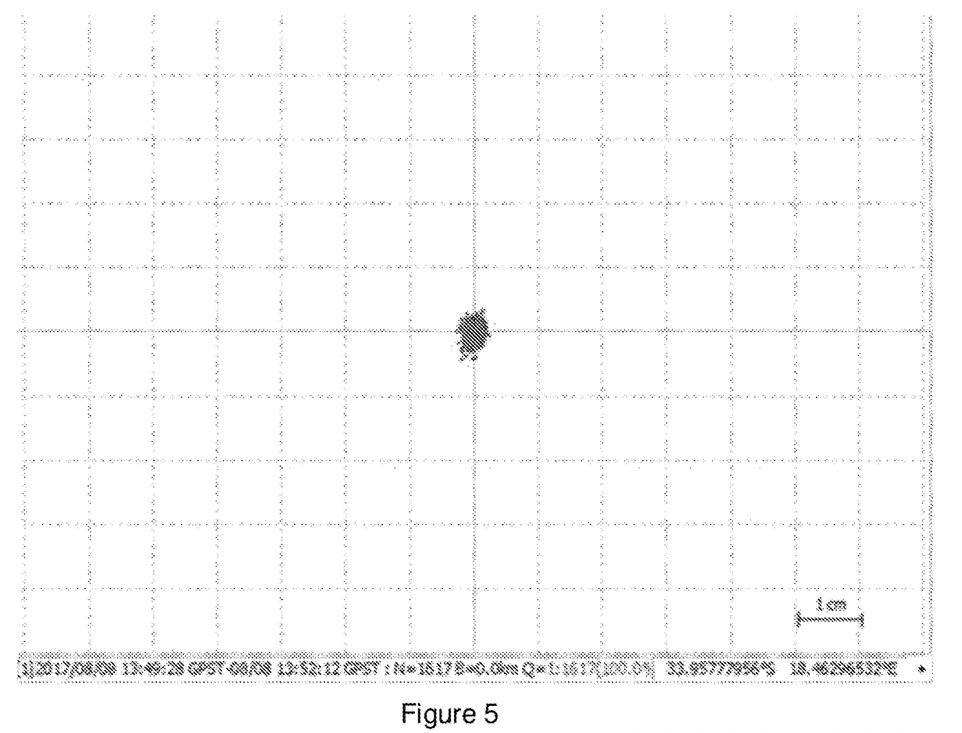
FIG. 5 is a plot which illustrates the results of a static position test performed using a GPS sensor in evaluation mode which indicate that position can be obtained within 1 cm.

Aspects of the disclosure may provide a sensor network which is synchronised by the one pulse per second (PPS) inherent to GPS (or similar) receivers. Motion sensing unit may operate independently of one another and in a distributed manner. Inertial measurement unit data may be augmented with RTK-GPS sensors on each limb to provide enhanced accuracy. Embodiments described herein may provide nanosecond accuracy, fault tolerance and theoretically unlimited numbers of motion sensing units. By augmenting IMU data points with RTK-GPS sensor-based data points from each limb (or other part of the body of interest), centimetre accuracy may be achieved, for example as illustrated in FIG. 5, (which may be competitive with a comparable static camera system). Placement of RTK-GPS sensors on each limb may enable direct measurement of the position of each relevant limb and thereby increase the robustness of the motion sensing unit during rapid motion.

The method and system as described herein may provide increased accuracy when compared to existing systems due to the placement of the sensors on each limb on the body of interest. By placing sensors on each limb of the body of interest direct measurement of the exact position of each limb may be possible. Placing the sensors on each limb on the body of interest may further eliminate the need to make assumptions about the motion of the limbs as in most IMU's which rely on an implicit relationship to derive the positions of the limbs of the body of interest. Placing sensors on each of the limbs of the body of interest may therefore mitigate the probability of inaccurate results and increase the overall robustness the system.

It is also foreseen that one or more of the motion sensing units may include a high power, active antenna, and that a wearable mechanical harness may be utilised to place sensing units in physical contact with the different parts of the body of interest.

Figure 6:
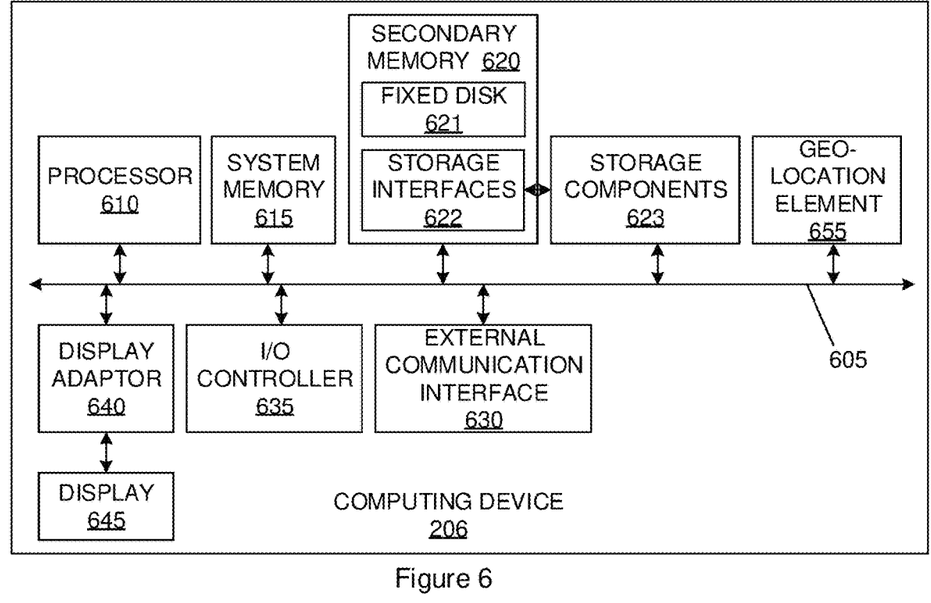
FIG. 6 illustrates an example of a computing device in which various aspects of the disclosure may be implemented.

FIG. 6 illustrates an example of a computing device (206) in which various aspects of the disclosure may be implemented. The computing device (206) may be embodied as any form of data processing device including a personal computing device (e.g. laptop or desktop computer), a server computer (which may be self-contained, physically distributed over a number of locations), a client computer, or a communication device, such as a mobile phone (e.g. cellular telephone), satellite phone, tablet computer, personal digital assistant or the like. Different embodiments of the computing device may dictate the inclusion or exclusion of various components or subsystems described below.

The computing device (206) may be suitable for storing and executing computer program code. The various participants and elements in the previously described system diagrams may use any suitable number of subsystems or components of the computing device (206) to facilitate the functions described herein. The computing device (206) may include subsystems or components interconnected via a communication infrastructure (605) (for example, a communications bus, a network, etc.). The computing device (206) may include one or more processors (610) and at least one memory component in the form of computer-readable media. The one or more processors (610) may include one or more of: CPUs, graphical processing units (GPUs), microprocessors, field programmable gate arrays (FPGAs), application specific integrated circuits (ASICs) and the like. In some configurations, a number of processors may be provided and may be arranged to carry out calculations simultaneously. In some implementations various subsystems or components of the computing device (206) may be distributed over a number of physical locations (e.g. in a distributed, cluster or cloud-based computing configuration) and appropriate software units may be arranged to manage and/or process data on behalf of remote devices.

The memory components may include system memory (615), which may include read only memory (ROM) and random access memory (RAM). A basic input/output system (BIOS) may be stored in ROM. System software may be stored in the system memory (615) including operating system software. The memory components may also include secondary memory (620). The secondary memory (620) may include a fixed disk (621), such as a hard disk drive, and, optionally, one or more storage interfaces (622) for interfacing with storage components (623), such as removable storage components (e.g. magnetic tape, optical disk, flash memory drive, external hard drive, removable memory chip, etc.), network attached storage components (e.g. NAS drives), remote storage components (e.g. cloud-based storage) or the like.

The computing device (206) may include an external communications interface (630) for operation of the computing device (206) in a networked environment enabling transfer of data between multiple computing devices (600) and/or the Internet. Data transferred via the external communications interface (630) may be in the form of signals, which may be electronic, electromagnetic, optical, radio, or other types of signal. The external communications interface (630) may enable communication of data between the computing device (206) and other computing devices including servers and external storage facilities. Web services may be accessible by and/or from the computing device (206) via the communications interface (630).

The external communications interface (630) may be configured for connection to wireless communication channels (e.g., a cellular telephone network, wireless local area network (e.g. using Wi-Fi™), satellite-phone network, Satellite Internet Network, etc.) and may include an associated wireless transfer element, such as an antenna and associated circuitry.

The computer-readable media in the form of the various memory components may provide storage of computer-executable instructions, data structures, program modules, software units and other data. A computer program product may be provided by a computer-readable medium having stored computer-readable program code executable by the central processor (610). A computer program product may be provided by a non-transient computer-readable medium, or may be provided via a signal or other transient means via the communications interface (630).

Interconnection via the communication infrastructure (605) allows the one or more processors (610) to communicate with each subsystem or component and to control the execution of instructions from the memory components, as well as the exchange of information between subsystems or components. Peripherals (such as printers, scanners, cameras, or the like) and input/output (I/O) devices (such as a mouse, touchpad, keyboard, microphone, touch-sensitive display, input buttons, speakers and the like) may couple to or be integrally formed with the computing device (206) either directly or via an I/O controller (635). One or more displays (645) (which may be touch-sensitive displays) may be coupled to or integrally formed with the computing device (206) via a display (645) or video adapter (640).

The computing device (206) may include a geographical location element (655) which is arranged to determine the geographical location of the computing device (206). The geographical location element (655) may for example be implemented by way of a global positioning system (GPS), or similar, receiver module. In some implementations the geographical location element (655) may implement an indoor positioning system, using for example communication channels such as cellular telephone or Wi-Fi™ networks and/or beacons (e.g. Bluetooth™ Low Energy (BLE) beacons, iBeacons™, etc.) to determine or approximate the geographical location of the computing device (206). In some implementations, the geographical location element (655) may implement inertial navigation to track and determine the geographical location of the communication device using an initial set point and inertial measurement data.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

Any of the steps, operations, components or processes described herein may be performed or implemented with one or more hardware or software units, alone or in combination with other devices. In one embodiment, a software unit is implemented with a computer program product comprising a non-transient computer-readable medium containing computer program code, which can be executed by a processor for performing any or all of the steps, operations, or processes described. Software units or functions described in this application may be implemented as computer program code using any suitable computer language such as, for example, Java™, C++, or Perl™ using, for example, conventional or object-oriented techniques. The computer program code may be stored as a series of instructions, or commands on a non-transitory computer-readable medium, such as a random access memory (RAM), a read-only memory (ROM), a magnetic medium such as a hard-drive, or an optical medium such as a CD-ROM. Any such computer-readable medium may also reside on or within a single computational apparatus, and may be present on or within different computational apparatuses within a system or network.

Flowchart illustrations and block diagrams of methods, systems, and computer program products according to embodiments are used herein. Each block of the flowchart illustrations and/or block diagrams, and combinations of blocks in the flowchart illustrations and/or block diagrams, may provide functions which may be implemented by computer readable program instructions. In some alternative implementations, the functions identified by the blocks may take place in a different order to that shown in the flowchart illustrations.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A computer-implemented method for capturing the motion of a body of interest, comprising:
   accessing a plurality of motion datasets including timestamped motion data points, each of the plurality of motion datasets being associated with a respective motion sensing unit at which the timestamped motion data points of that motion dataset are generated, wherein each of the plurality of motion sensing units is configured to be in physical contact with a different part of a body of interest and each of the plurality of motion data sensing units includes a plurality of disparate sensors and wherein each motion dataset includes timestamped motion data points from each of the plurality of disparate sensors which relate to motion of that motion sensing unit and global navigation satellite systems-based motion data points;
   wherein each of the plurality of motion sensing units includes a respective satellite network sensor arranged to receive signals transmitted from a global or regional navigation satellite systems network and wherein each timestamped motion data point is timestamped independently at the motion sensing unit at which it is generated using a clock time that is synchronized across the plurality of motion sensing units using the satellite systems network and the satellite network sensor of that motion sensing unit;
   accessing a reference dataset including reference data points having been measured at a base unit, wherein the position of the base unit is fixed;
   using the reference dataset to correct errors present in the motion datasets, wherein using the reference dataset to correct errors includes applying real time kinematic techniques to enhance precision of the global navigation satellite systems-based motion data points;
   processing the timestamped motion data points to generate a kinematic model which describes motion of the respective parts of the body of interest; and,
   outputting the kinematic model.

2. The method of claim 1, wherein the satellite systems network is a global navigation satellite systems network.

3. The method of claim 1, including pre-processing the timestamped motion data points using a pre-processing algorithm.

4. The method of claim 3, wherein pre-processing the timestamped motion data points includes, for each of the plurality of motion datasets, inputting the timestamped motion data points from the disparate sensors into a filtering algorithm which outputs a single series of filtered motion data points for that motion dataset.

5. The method of claim 3, including applying a structural model associated with the body of interest to the timestamped motion data points, wherein the structural model defines theoretical kinematic constraints associated with respective parts of the body of interest by identifying invalid timestamped motion data points and wherein applying the structural model includes inputting the theoretical kinematic constraints into the filtering algorithm as additional information during filtering of the motion data points.

6. The method of claim 5, wherein the body of interest is a human or animal body, and wherein the structural model is a skeletal model.

7. The method of claim 3, wherein the pre-processing algorithm is a non-linear least squares estimation algorithm.

8. A system for capturing the motion of a body of interest, comprising:
a processor and a memory configured to provide computer program instructions to the processor to execute functions of components;
a motion dataset accessing component for accessing a plurality of motion datasets including timestamped motion data points, each of the plurality of motion datasets being associated with a respective motion sensing unit at which timestamped motion data points of that motion dataset are generated, wherein each of the plurality of motion sensing units is configured to be in physical contact with a different part of a body of interest and includes a plurality of disparate sensors and wherein each motion dataset includes timestamped motion data points from each of the plurality of disparate sensors which relate to motion of that motion sensing unit and global navigation satellite systems-based motion data points;
wherein each motion sensing unit includes a satellite network sensor arranged to receive signals transmitted from a global or regional navigation satellite systems network and wherein each timestamped motion data point is timestamped at the motion sensing unit at which it is generated using a clock time that is synchronized across the plurality of motion sensing units using the satellite systems network;
a correction component including:
a reference dataset accessing component arranged to access a reference dataset including reference data points having been generated at a base unit having a fixed position; and
an error correcting component arranged to use the reference dataset to correct errors introduced into the motion datasets to enhance precision of the global navigation satellite systems-based motion data points;
a processing component for processing the timestamped motion data points to generate a kinematic model which describes motion of the respective parts of the body of interest; and,
a model outputting component for outputting the kinematic model.

9. The system of claim 8, including a plurality of motion sensing units, wherein each of the plurality of motion sensing units includes a respective plurality of disparate sensors and wherein each of the plurality of motion datasets includes respective timestamped motion data points from each of the plurality of disparate sensors for that motion sensing unit.

10. A system including a motion sensing unit for capturing the motion of a body of interest in a motion dataset and configured to be in physical contact with a part of the body of interest, the motion sensing unit comprising:
a plurality of disparate sensors for generating timestamped motion data points from each of the plurality of disparate sensors which relate to motion of the sensing unit for inclusion in the motion dataset;
a satellite network sensor for receiving a satellite network signal including timing information and having been transmitted from a global or regional navigation satellite systems network for providing global navigation satellite systems-based motion data points for inclusion in the motion dataset;
a clock synchronisation component for using the satellite network signal to synchronise a local clock time maintained by the motion sensing unit with clock times of a plurality of other motion sensing units in a sensor network;
a timestamping component for timestamping the motion data points to generate timestamped motion data points; and,
a providing component for providing the motion dataset including the timestamped motion data points to a computing device,
wherein the motion dataset is provided to the computing device for processing together with motion datasets from the other motion sensing units in the sensor network to generate a kinematic model which describes motion of the respective parts of the body of interest, including correcting errors present in the motion datasets using a reference dataset including reference data points having been measured at a base unit with a fixed position to correct errors by applying real time kinematic techniques to enhance the precision of the global navigation satellite systems-based motion data points.

11. The system of claim 10, including the computing device, comprising:
a processor and a memory configured to provide computer program instructions to the processor to execute functions of components;
a motion dataset accessing component for accessing a plurality of motion datasets including timestamped motion datapoints, each of the plurality of motion datasets being associated with a respective one of the plurality of motion sensing units at which timestamped motion data points of that motion dataset are generated, wherein each of the plurality of timestamped motion data points is timestamped independently at the motion sensing unit at which it is generated using a clock time that is synchronized across the plurality of motion sensing units using the satellite systems network and the satellite network sensor of that motion sensing unit, wherein each motion dataset includes timestamped motion data points from each of the plurality of disparate sensors which relate to motion of that motion sensing unit and global navigation satellite systems-based motion data points;
a correction component including:
a reference dataset accessing component arranged to access a reference dataset including reference data points having been generated at a base unit having a fixed position; and an error correcting component arranged to use the reference dataset to correct errors introduced into the motion datasets to enhance precision of the global navigation satellite systems-based motion data points;

a processing component for processing the timestamped motion data points to generate a kinematic model which describes motion of the respective parts of the body of interest; and, a model outputting component for outputting the kinematic model.

* * * * *